United States Patent [19]

Voykin

[11] Patent Number: 4,852,553

[45] Date of Patent: Aug. 1, 1989

[54] SELF-ADMINISTERING REFLEX MASSAGE THERAPY APPARATUS

[76] Inventor: William J. Voykin, 542 Baker Street, Nelson, British Columbia V1L 4H9, Canada

[21] Appl. No.: 171,580

[22] Filed: Mar. 22, 1988

[51] Int. Cl.[4] .......................... A61H 1/00; A61H 7/00; A61H 15/00; A61F 5/00

[52] U.S. Cl. .................................... 128/25 B; 128/581

[58] Field of Search .................... 128/582, 329 A, 779, 128/60, 61, 62 R, 67, 44, 25 B, 586, 587, 596, 601, 602, 581, 24.3, 24.4; 272/94, 95; 40/518, 611

[56] References Cited

U.S. PATENT DOCUMENTS

| | | | |
|---|---|---|---|
| 1,702,531 | 2/1929 | Ambill | 128/587 |
| 1,711,850 | 5/1929 | Rake | 40/518 |
| 2,168,842 | 8/1939 | Kestovey et al. | 128/61 |
| 4,091,552 | 5/1978 | Dickerson | 40/518 |
| 4,109,661 | 8/1978 | Fukuoka | 128/582 |
| 4,223,966 | 11/1980 | Jakahashi | 128/60 |
| 4,632,095 | 12/1986 | Libin | 128/60 |
| 4,694,831 | 9/1987 | Saltzer | 128/582 |
| 4,726,132 | 2/1988 | Ernest | 40/611 |

FOREIGN PATENT DOCUMENTS

| | | | |
|---|---|---|---|
| 2619410 | 11/1976 | Fed. Rep. of Germany | 128/582 |
| 2749138 | 5/1979 | Fed. Rep. of Germany | 128/581 |
| 2574288 | 6/1986 | France | 128/329 A |
| 0936913 | 6/1982 | U.S.S.R. | 128/329 A |
| 2123696 | 2/1984 | United Kingdom | 128/25 B |

*Primary Examiner*—Edgar S. Burr
*Assistant Examiner*—Kimberly L. Asher
*Attorney, Agent, or Firm*—Fetherstonhaugh & Co.

[57] ABSTRACT

A foot zone reflex self-administering therapy apparatus, comprising a display board adapted to display foot reflexology zones corresponding to anatomical areas of the body and stimulating members adapted to be placed on the display board at a zone corresponding to an anatomical area of the body requiring therapy. The user's foot is placed on the display board over the stimulating members in order to apply a kneading, massaging action to the corresponding zone of the user's foot.

5 Claims, 4 Drawing Sheets

SELF-ADMINISTERING REFLEX MASSAGE THERAPY APPARATUS

FIELD OF THE INVENTION

This invention relates to foot massage apparatus and more particularly to a self-administering massage therapy apparatus adapted to take advantage of foot reflex zone therapy.

BACKGROUND OF THE INVENTION

The topological relationship between the foot reflexes and the organs of the body have been studied for a number of years. Clinical and scientific experimentation have resulted in the creation of foot reflexology area charts. Reflex zone therapy involving massaging of the foot zones shown on these charts can be utilized for the treatment of specific, or general corresponding organic systems of the body.

Stimulation of these foot zones may be accomplished using a number of methods: by directing pressure with the fingers or other instruments, or by using heat or electric impulses applied at each zone. Patients may themselves stimulate these zones through simple finger pressure or stimulation with a device. Zone stimulation has been found to be remarkable in its effectiveness for the relief of pain or treatment of disease.

Although the evolution of the foot reflexology area charts have been perfected in recent years, the location of these reflex zones remain basically the same and are inherently standard in all humans.

Previous charts were made for therapists as an aid to reference when facing the feet of their patient. So as to make do-it-yourself therapy practical, the foot chart had to be reversed.

The concept of massage pressure on the soles of the feet is not totally new, since there are many professional semi-professional and lay persons that practice reflex zone therapy in some degree. In addition, there have been various foot massage apparatus. For example, foot rollers, rubbing mats and insoles with miniature fingers-like protrusions and other devices with massage in mind. These devices may be beneficial to some degree. Best results are obtained from professionally-trained therapists but such professional treatment is often rare and costly and, in many areas, not available or unknown.

SUMMARY OF THE INVENTION

There is therefore a requirement for a self-administering foot zone reflex therapy apparatus which can provide therapeutic relief without the user having to study the theory of foot zone reflex therapy.

Another object of the present invention is to provide the self-administering foot zone reflex therapy apparatus which can be used conveniently and easily in the privacy of the user's home.

The self-administering foot zone reflex therapy apparatus comprises a housing assembly with a smooth-surfaced display area having charts and diagrams of the known reflex areas or reflex zones of the feet. A variety of stimulators with protrusions, knobs or ridges on their top side are provided. These stimulators are designed to be applicable to most shapes and sizes of feet. Other stimulators are designed to be used on the lateral, medial and top portions of the foot. The stimulator is pressed onto the desired area on the foot chart which is on the surface of the board. The user then applies his foot with pressure over the stimulator with a kneading, massaging action.

According to an aspect of this invention, there is provided a self-administering foot zone reflex therapy apparatus, comprising:

display means adapted to display foor reflexology zones corresponding to anatomical areas of the body;

stimulating means adapted to be placed on the display means at a zone corresponding to an anatomical area of the body requiring therapy whereby the user's feet are placed on the display means over the stimulating means in order to apply a kneading, massaging action to the corresponding zone of the user's foot.

DESCRIPTION OF THE DRAWINGS

Particular embodiments of the invention will be understood in conjunction with the accompanying drawings in which.

DESCRIPTION OF THE PREFERRED EMBODIMENTS

Figure 1:
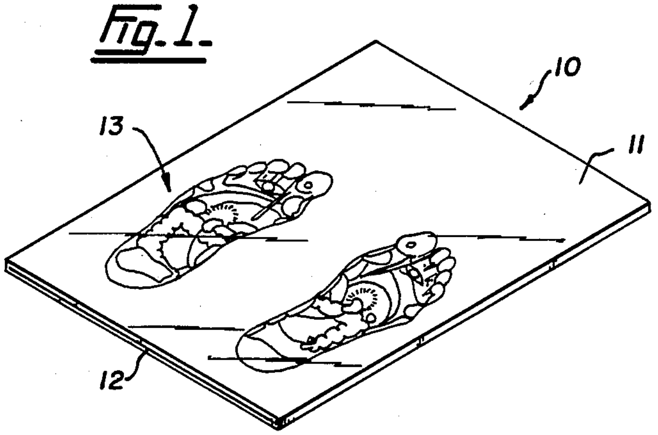
FIG. 1 is a perspective view of a board assembly according to a first embodiment of the present invention.

Referring now to FIG. 1 we have shown a board like assembly 10 which can be made of a clear layer of plexiglass 11, and which may include a slot 12 to permit insertion of charts and diagrams 13 of the known reflex areas or reflex zones of the feet. Various charts can be provided to allow for variations in the size of the user's feet. In addition, board 10 can be imprinted with a separate chart on each surface such that one surface would depict reflex zones at the sole of the feet and the other surface would indicate reflex zones located on the lateral and medial aspects of the feet.

FIGS. 2*a* to 2*e* display various types of stimulators which are used in conjunction with the board of FIG. 1 for administering foot reflex therapy. Various stimulators can be used and need not be limited to those shown in FIGS. 2*a*, 2*b*, 2*c*, 2*d* and 2*e*. In general, these stimulators have protrusions, knobs or ridges on there top side and a suction cup on the bottom side. These stimulators would, of course, be designed so as to be applicable to most shapes and sizes of feet. The stimulators of FIGS. 2*a*, 2*b*, 2*c* and 2*e* would be used for stimulating reflex zones such as shown at reference numeral 13 of FIG. 1 whereas the stimulator shown in FIG. 2*d* would be used on the lateral, medial and top of the foot.

Figure 2A:
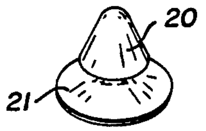
FIGS. 2*a* to 2*e* represent perspective views of various stimulators that can be used with the display board shown in FIG. 1.
Figure 2B:
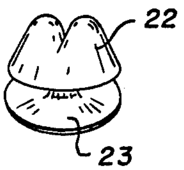

The stimulator of FIG. 2*a* is comprised of a cone shaped body 20 secured to a suction cup 21. The stimulator of FIG. 2*b* is comprised of two cone shaped bodies 22 secured together and attached to a suction cup 23. The shape of the stimulator bodies permit a subdermal penetrating effect to the reflex zone area of the feet when the user applies pressure to the stimulator.

Figure 2C:
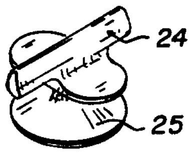

The stimulator of FIG. 2*c* includes an elongated body 24 which permits the user to reach areas located between the toes. Body 24 is secured to a suction cup 25. The purpose of the suction cups is to permit the stimulators to adhere to the smooth surface of the board and to stabilize the stimulator when a user applies pressure onto the head of the stimulator.

Figure 2D:
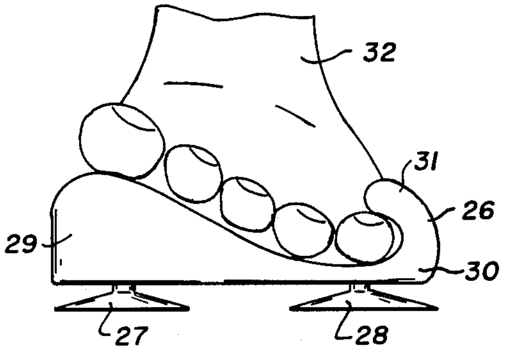

Stimulator 26 of FIG. 2*d* depicts another type of stimulator designed to treat the reflex areas on the lateral and medial aspects of the foot. Similarly, suction cups 27 and 28 are used to secure the stimulator to the board. Stimulator 26 has an elongated body with a first side edge 29 sloping towards a second side edge 30. A hook shaped ridge 31 extending upwardly from side edge 30 will achieve the required stimulation since when user applies pressure onto the body of the stimulator, the foot 32 will slide laterally against ridge 31.

Figure 2E:
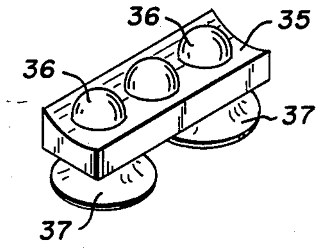

Stimulator 35 of FIG. 2*e* includes a series of rollers 36 which provide a rolling action massage to permit a user to cover a wider reflex zone area. Stimulator 35 is similarly secured to board 10 of FIG. 1 by means of a series of suction cups 37.

The body parts of these stimulators can be made of solid material, such as wood, plastic, metal or ceramic materials while the suction cup attachments would be formed from flexible plastic or like material.

Figure 3:
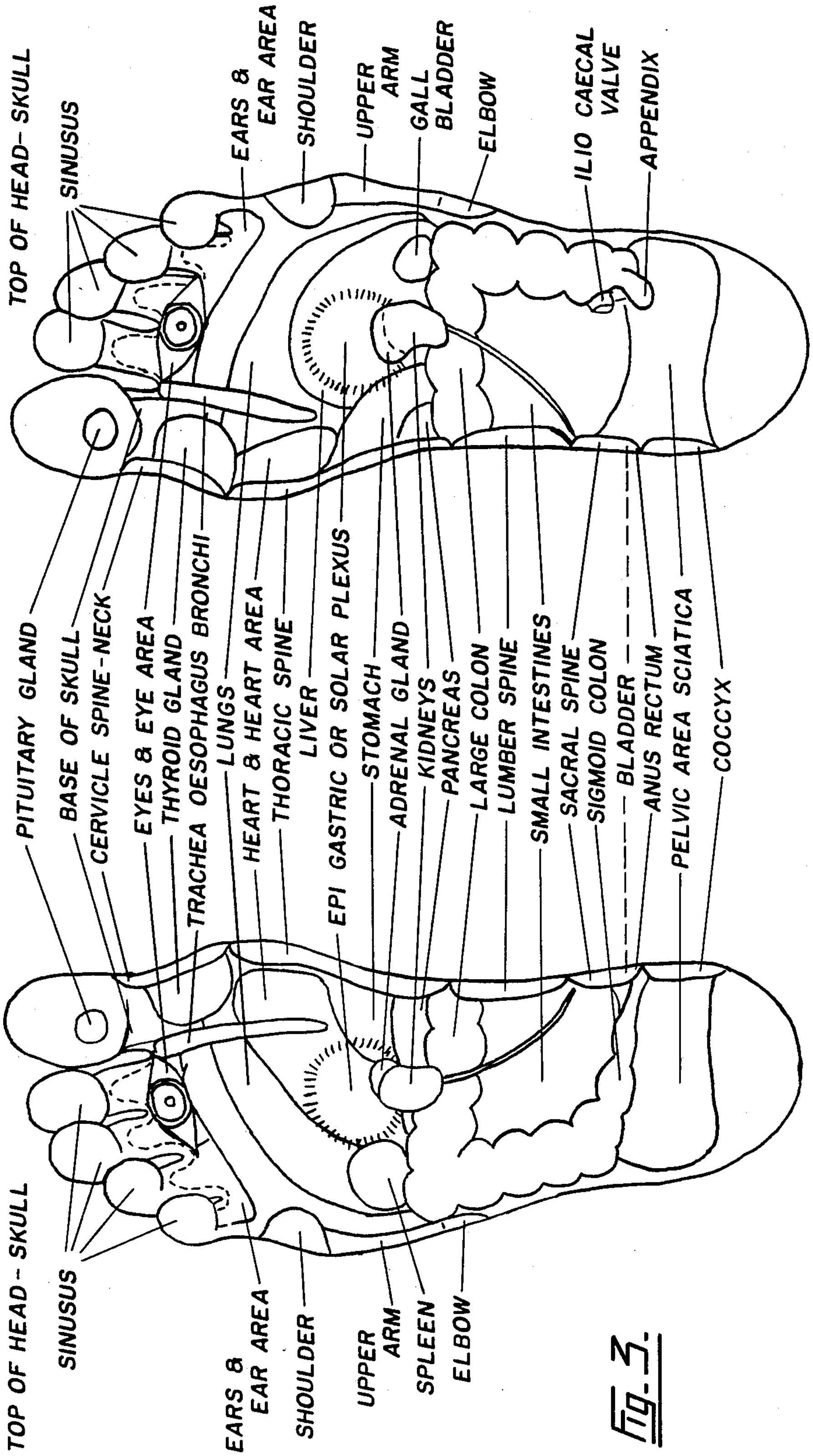
FIG. 3 is an illustration of the foot reflex zones.
Figure 4A:
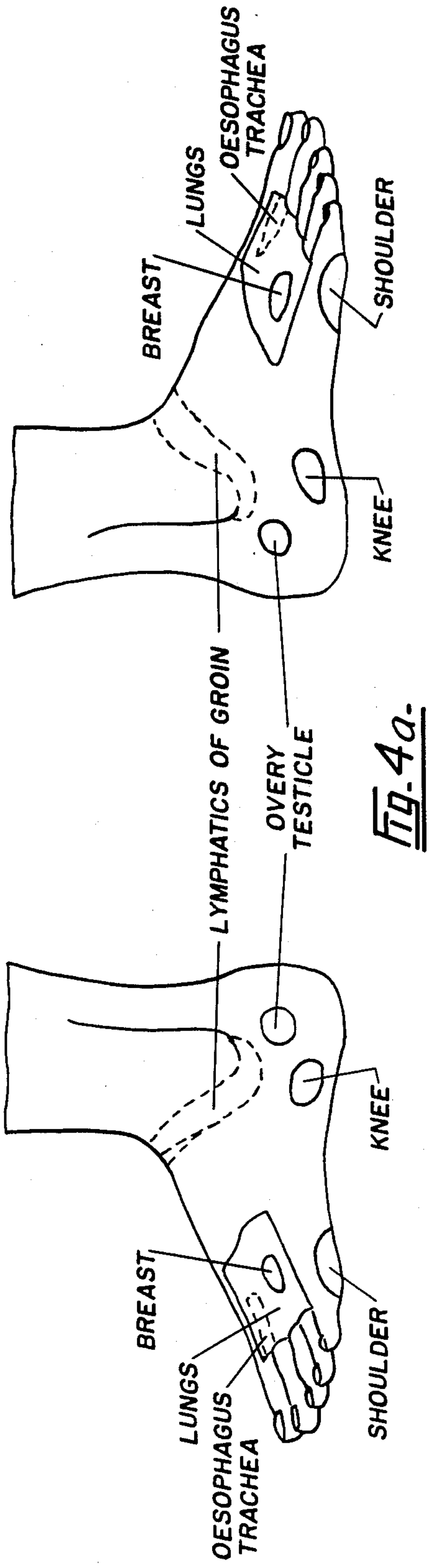
FIGS. 4*a* and 4*b* represent additional foot reflexology charts displaying zones corresponding to other anatomical areas of the body.
Figure 4B:
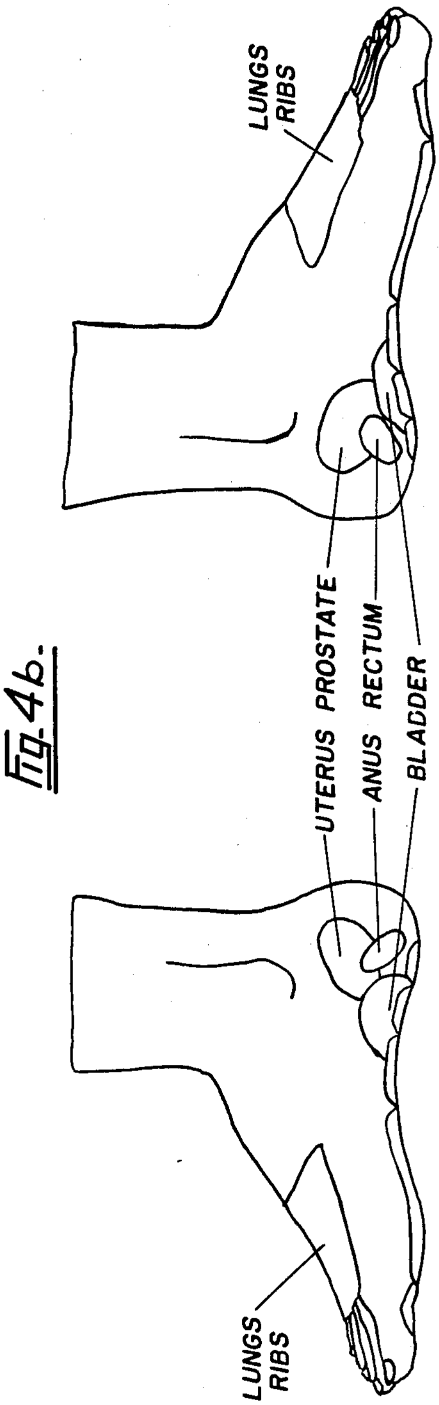

Referring now to FIG. 3 we have shown a foot reflex therapy chart which has been reversed to allow a user to perform therapy. Although these charts are well known, the chart of FIG. 3 is reversed from those commonly used by therapists since a therapist would face the patient's feet and accordingly the location of the reflex zones would be opposite those seen by a patient. The chart of FIG. 3 displays the reflex zones corresponding to anatomical areas of the body. Accordingly, in use, a user would position a stimulator on the chart at an area corresponding to an anatomical area of the body requiring therapy. The user's foot or feet would then be placed on the corresponding display area and the user would then apply pressure onto the body of the stimulator in a kneading, massaging action.

Other reflex areas on the lateral and medial aspects of the foot are displayed in FIGS. **4*a* and 4*b* respectively. These areas can be massaged by using a stimulator such as shown in FIG. 2*d***.

The use of a board having two sheets of plastic glass or other similar material to sandwich the foot chart is the first preferred embodiment. The smooth, hard surface of the plexiglass represent a good base for the suction cups. Additionally, the plexiglass protects the charts.

As an alternative, the plexiglass base can be provided with a series of small apertures or holes drilled over the reflex zones of the chart. The stimulators would then be provided with protrusions on their base to fit in the apertures or holes of the board.

Alternatively, a metallic surface board for use with stimulators having a magnetic attachment can be used.

Figure 5:
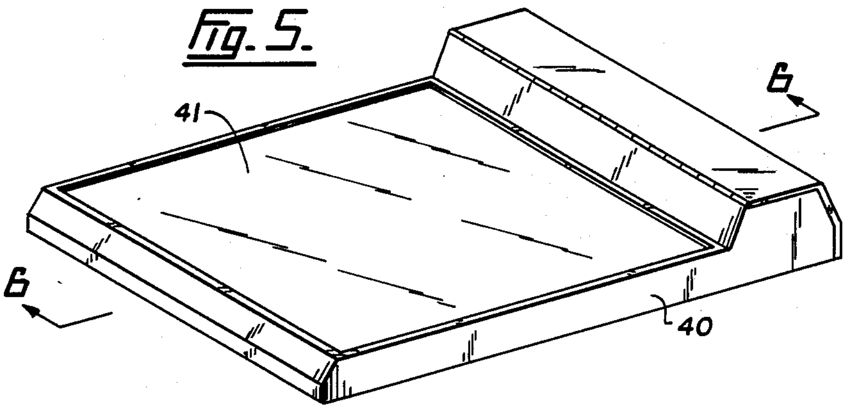
FIGS. 5 is an isometric view of a board assembly according to a second embodiment of the invention.
Figure 6:
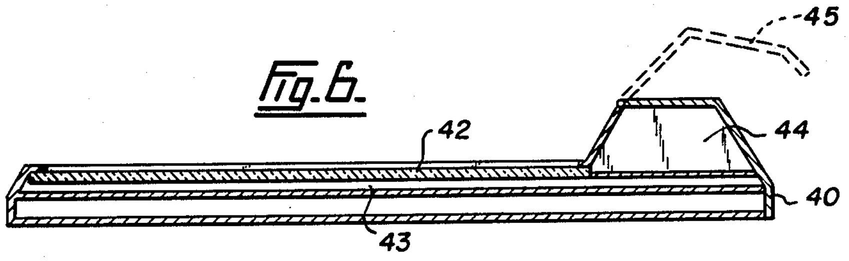
FIG. 6 is a sectional side view thereof.

Referring now to FIG. 5, we have shown a front isometric view of a display board assembly according to a second embodiment of the present invention. The display assembly is comprised of a housing 40 having a display area 41 consisting of a clear sheet of plexiglass 42 embedded in housing 40 and adapted to allow viewing of a specific chart which would be inserted underneath plexiglass sheet 42 in slot 43, as depicted in FIG. 6. Plexiglass sheet 42 and housing assembly 40 are, of course, strong enough to support the user's weight. A storage compartment 44, having a lid 45, is provided for storing charts and stimulators.

Figure 7:
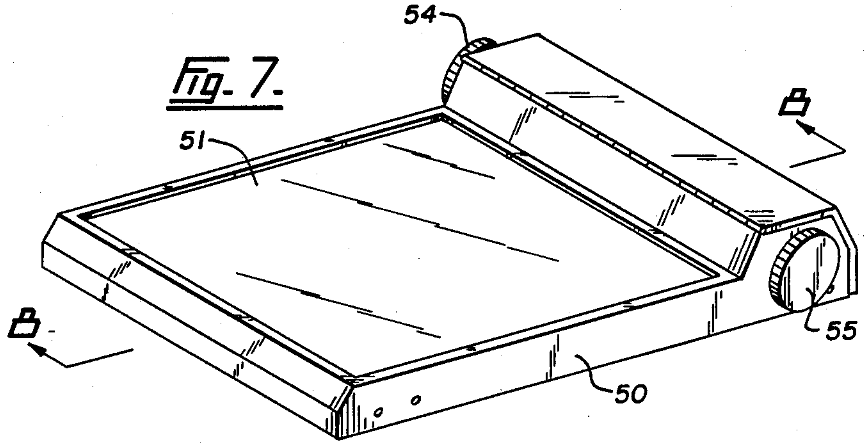
FIG. 7 is an isometric view of a board assembly according to a third embodiment of the invention.
Figure 8:
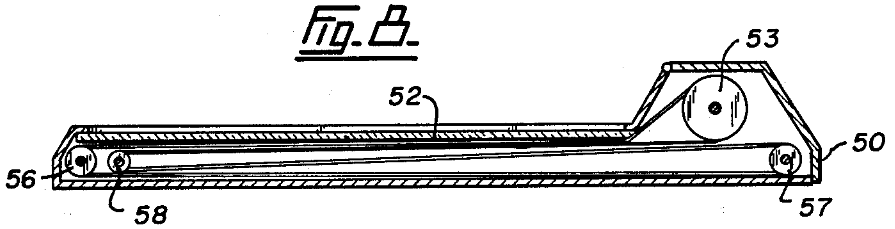
FIG. 8 is a sectional view thereof.

Referring now to FIGS. 7 and 8, we have shown a display board assembly according to a third embodiment of the present invention. The display assembly is similarly comprised of a housing 50, having a display area 51 consisting of a clear sheet of plexiglass 52 embedded in housing 50. However, in this embodiment, a series of rollers allow a user to change the type of chart being displayed. These rollers include a driving roller 53 provided with knobs 54 and 55 which allow a user to rotate the rollers to display various charts on an endless belt looped about the rollers.

In this embodiment, charts are led from driving roller 53 below plexiglass sheet 52 to a first driven roller 56 positioned at the front end of housing 50, then on to a second driven roller 57 at the rear of housing 50 and then back to a third driven roller 58 at the front end of housing 50 and back to the main driving roller 53. The use of multiple rollers arranged in such a manner allows for a longer endless belt having a greater length on which charts can be drawn.

It may also be advantageous to make single system charts, i.e. digestive system, respiratory system, endocrine system, etc. These charts would be interchanged as desired by the user. In addition, these charts would show distinctly what the user is looking for, since the foot chart disclosed in FIG. 3 show some reflex zones which overlap one another.

As will be apparent to those skilled in the art, in light of the foregoing disclosure, many alterations and modifications are possible in the practice of this invention without departing from the spirit or scope thereof. Accordingly, the scope of the invention is to be construed in accordance with the substance defined by the following claims.

The embodiments of the invention in which an exclusive privilege or property is claimed are defined as follows:

1. A foot zone reflex self-administering therapy apparatus, comprising:
- a display housing to display foot reflexology zone charts, said housing having a display area for viewing a single chart at at time and a storage area for storing said charts;
- said display area comprising a transparent plastic sheet positioned above a chart holding cavity;
- said storage area comprising a compartment with a hinged cover; and
- stimulating members comprising a body having pressure projections and attachment means to allow said stimulating members to be releasably positioned on said transparent sheet in patterns according to the various zones displayed on said single chart visible in said chart holding cavity through said transparent plastic sheet whereby a user's foot can be placed on said positioned stimulating means in other to apply a kneading, massaging action to the user's foot.

2. A self-administering therapy apparatus as defined in claim 1 wherein said attachment means is a suction cup.

3. A self-administering therapy apparatus as defined in claim 1 wherein said pressure projections are cone shaped.

4. A self-administering therapy apparatus as defined in claim 1 wherein said stimulating member comprises a body having a slanted surface with a raised edge on the lower side of said surface, such that reflex zones on the lateral, medial and top regions of the foot can be stimulated.

5. A self-administering therapy apparatus as defined in claim 1 wherein said pressure projections are rollers rotatably attached to the body of said stimulating member.

* * * * *